(12) United States Patent
Perot

(10) Patent No.: US 7,854,889 B2
(45) Date of Patent: Dec. 21, 2010

(54) PROCESS FOR DECONTAMINATION BY RADIATION OF A PRODUCT SUCH AS A PACKAGING CONTAINING MEDICAL DEVICES

(75) Inventor: Frédéric Perot, Saint Paul de Varces (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/006,943

(22) Filed: Jan. 8, 2008

(65) Prior Publication Data

US 2008/0175752 A1    Jul. 24, 2008

(30) Foreign Application Priority Data

Jan. 9, 2007  (FR) .................................. 07 00117

(51) Int. Cl.
*A61L 2/08* (2006.01)
(52) U.S. Cl. .................. 422/22; 250/455.11; 250/493.1
(58) Field of Classification Search .................. 422/22, 422/24, 186, 186.3; 250/496.1, 455.11, 493.1, 250/497.1
See application file for complete search history.

(56) References Cited

U.S. PATENT DOCUMENTS

| | | | |
|---|---|---|---|
| 2,724,059 A | 11/1955 | Gale | |
| 2,957,078 A * | 10/1960 | Gale | 250/393 |
| 4,010,374 A | 3/1977 | Ramler | |
| 4,652,763 A | 3/1987 | Nablo | |
| 5,496,302 A | 3/1996 | Minshall et al. | |
| 6,203,755 B1 | 3/2001 | Odland | |
| 2005/0078789 A1 | 4/2005 | Miller | |
| 2006/0054523 A1 | 3/2006 | Porret et al. | |

FOREIGN PATENT DOCUMENTS

| | | |
|---|---|---|
| EP | 2 055 321 A1 | 5/2009 |
| WO | WO 2004/110157 A | 12/2004 |
| WO | WO 2004/110157 A2 | 12/2004 |

OTHER PUBLICATIONS

International Search Report for International Application No. PCT/US2008/000256 dated Oct. 16, 2008.
European Search Report, EP 2 055 321 A1, Dated Mar. 23, 2009.

* cited by examiner

*Primary Examiner*—Sean E Conley
(74) *Attorney, Agent, or Firm*—David M. Fortunato; Cohen Pontani Lieberman & Pavane LLP

(57) ABSTRACT

A process for decontamination by radiation of a product. The process comprises at least one exposing step during which at least a first part of the product is exposed to a first radiation level, and at least a second part of the product is exposed to a second radiation level. The invention also relates to an equipment suitable for such a process.

12 Claims, 4 Drawing Sheets

PROCESS FOR DECONTAMINATION BY RADIATION OF A PRODUCT SUCH AS A PACKAGING CONTAINING MEDICAL DEVICES

BACKGROUND OF THE INVENTION

1. Field of the Invention

The present invention relates to a new process for the decontamination by radiation of a product, in particular a packaging containing medical devices.

2. Description of the Related Art

The conditions of sterility in which certain stages of the handling or transportation of items or instruments intended for medical use are to be performed are extremely strict, particularly in the pharmaceutical industry. It is therefore extremely important to produce packaging compatible with such requirements.

In the present application, the expression "radiation screen" is to be understood as being a screen capable of reflecting or absorbing substantially all the kinetic energy of the electrons from an electron beam, and therefore of preventing these electrons from passing through the said screen.

In the present application, the expression "semi-permeable radiation screen" is to be understood as being a screen capable of partially reflecting or absorbing the kinetic energy of the electrons from an electron beam, and therefore of allowing only a restricted percentage of these electrons to pass through the screen.

In the present application, the expression "selectively impervious material" is to be understood as meaning that the material is designed, in terms of structure, to control any exchange between the inside of the packaging and its external environment. This means, among other things, that the packaging is impervious to contamination by micro-organisms, bacteria and/or a biologically active material likely to come into contact with the packaging while it is being handled, while at the same time remaining permeable to a sterilization or decontamination gas, for example of the ETO (ethylene oxide) type.

Packagings for items that are or may be sterilized by a sterilization gas are known. In the case of medical items such as syringes, these packaging usually comprise a tub sealed with a cover sheet made of a selectively impervious material. An example of such a packaging is shown on FIGS. 1 and 2. FIG. 1 is a cross section view of a product which is a packaging 1 comprising a tub 2 and a cover sheet 3, usually made of a selectively impervious material, the cover sheet 3 being sealed to the tub 2 so as to seal the tub 2 imperviously. The tub 2 comprises a plurality of medical items under the form of syringes bodies 4. In the example shown, the syringes bodies 4 are received in holes designed on a plate placed inside the tub 2 and bearing on a rim provided on the inner wall of the tub 2.

As appears clearly from FIG. 2, which is a top view of the packaging 1 of FIG. 1, the cover sheet 3 defines a central area 5, located more or less above the syringe bodies 4, which are shown in dashes, and a peripheral outline 6 surrounding this central area 5. The peripheral outline 6 corresponds more or less to the sealing portion of the cover sheet 3 on the tub 2.

Usually, in order to proceed with the sterilization of the items 4 contained in such a packaging 1, a sterilization gas, for example of the ethylene oxide type, enters the tub 2 through the cover sheet 3 of selectively impervious material. The tub 2 containing the sterilized items 4 is then placed in a protective bag so that the tub 2 can be transported. To proceed with the subsequent handling step, for example the filling of the syringe bodies 4, the protective bag needs to be opened. The packaging 1, which may then be contaminated, needs to be decontaminated before it is taken, for example, into a sterile room.

Such decontamination can be achieved using multidirectional irradiation by an electron beam developing enough energy that when it has passed through the cover sheet, it delivers a dose of irradiation of, for example, 25 kGy. This means that it can be taken that the selectively impervious material has been decontaminated throughout its thickness, particularly at the sealing portion located at the peripheral outline 6 of the cover sheet 3 at the interface between the tub 2 and the material. Indeed, it is very important that the peripheral outline 6 of the cover sheet 3, the downside 6a (see FIG. 1) of which is not in contact with the sealed atmosphere of the inside of the tub 2, unlike the downside 5a of the central area 5 of the cover sheet 3, be totally decontaminated. As far as the rest of the tub 2 is concerned, namely the bottom and lateral walls of said tub 2, the combination of the density and thickness of said tub 2 is such that it stops these electrons.

This type of decontamination is not, however, suitable for every type of product transported in the packaging. This is because the electron beam passing through the sheet of selectively impervious material carries the risk of altering or adversely affecting the material of which the syringes or products placed in the tub are made, for example glass. The electron beam can also generate ozone from the oxygen in the air contained in the tub. The generated ozone carries the risk of polluting the atmosphere and of adversely affecting the active products used to fill the syringes and/or, for example, the rubber components present in the tub such as the caps on the needles mounted on the syringes.

There is, therefore, a need for a process of sterilization of a product, in particular of a packaging containing medical devices as described above, that would allow the efficient decontamination of the peripheral outline of the product while preserving the integrity of the items stored in the product or the internal part of the product, regardless of the shape of the product.

SUMMARY OF THE INVENTION

In accordance with one embodiment, the present invention aims at satisfying this need by proposing a process for decontamination by radiation of a product, characterized in that it comprises at least one exposing step during which at least one radiation generator is used to expose at least a first part of the product to a first radiation level and at least a second part of the product to a second radiation level.

The process of an embodiment of the invention allows the efficient decontamination of a first part of a product, such as a packaging peripheral outline, and of a second part of the product such as the central area defined by the peripheral outline, without altering the integrity of the product contained in the packaging, and regardless of the shape of the product and/or packaging. The product to be decontaminated can also be different from a packaging. It can be a product for which the inside integrity needs to be preserved by preventing electron radiation from reaching it.

In an embodiment of the process of the invention, during the exposing step, the first part and second part are successively exposed to said first and second radiation levels.

In the present application, the terms "high, low, higher and lower" used to compare the radiation levels emitted by the radiation generators or received by the product correspond to the radiation intensity, respectively, received and emitted.

In an embodiment of the process of the invention, during the exposing step, said first part and second part are simultaneously exposed to the first and second radiation levels.

In an embodiment of the process of the invention, at least one side of the product comprises a central area and a peripheral outline, the first part of the product comprises at least the peripheral outline and the second part of the product comprises at least the central area, the first radiation level being higher than the second radiation level.

In an embodiment of the process of the invention, the first and second radiation levels are reached by using at least a high radiation generator and a low radiation generator, respectively, emitting high and low radiation levels.

In an embodiment of the process of the invention, the first and second radiation levels are reached by using at least a long radiation exposition period and a short radiation exposition period respectively toward the first and second parts of the product.

In an embodiment of the process of the invention, the short and long radiation exposition periods are reached by using two different displacement speeds of the product relative to the radiation generator.

In an embodiment of the process of the invention, the first and second radiation levels are reached by using at least one variable radiation generator set in order to emit a first radiation level toward the first part of the product and a second radiation level toward said second part of the product.

In an embodiment of the process of the invention, the first and/or second radiation levels are reached by using a radiation generator having a shape roughly similar to the first and/or second part(s) of the product.

In another embodiment of the process of the invention, the first and second radiation levels are reached by using at least a high radiation generator to emit high radiation level toward the product and placing a radiation screen or semi-permeable radiation screen between the high radiation generator and the second part of the product.

The radiation screen or semi-permeable radiation screen may be fixed with respect to the second part of the product.

Alternatively, the high radiation generator is mobile with respect to the product and the radiation screen or semi-permeable radiation screen is removably fixed to the high radiation generator.

In another embodiment of the process of the invention, the first and second radiation levels are reached by placing at least a first and a second radiation generator at specific angle positions with respect to, respectively, the first and second parts of the product.

Another aspect of the invention is an equipment for radiation decontamination of a product, the equipment comprising at least one radiation generator able to emit a predetermined quantity of radiations during a predetermined period of time toward the product, characterized in that it further comprises radiation setting means to set at least a first radiation level received by a first part of the product and a second radiation level received by a second part of the product.

The radiation setting means may comprise a radiation screen or semi-permeable radiation screen located between the radiation generator and the second part of the product.

The radiation screen or semi-permeable screen may be fixed with respect to the second part of the product.

In an embodiment of the invention, the equipment comprises a high radiation generator and a low radiation generator respectively emitting the first radiation level and the second radiation level.

In an embodiment of the invention, the equipment comprises displacement means of the product relative to the generator, the displacement means being adjustable to have a low speed for the radiation of one of the first or second part and a high speed for the radiation of the other part.

In another embodiment of the invention, the equipment comprises a variable radiation generator set in order to emit a first radiation level toward the first part of the product and a second radiation level toward the second part of the product.

In another embodiment of the invention, the equipment comprises at least a radiation generator having a shape roughly similar to the first and/or second part of the product.

In another embodiment of the invention, the equipment comprises a first and a second radiation generators located at specific angle positions with respect to, respectively, the first and second parts of the product.

BRIEF DESCRIPTION OF THE DRAWINGS

Other features and advantages will become apparent from the detailed description given hereinafter, given by way of example with reference to the appended drawings in which.

DETAILED DESCRIPTION OF THE PRESENTLY PREFERRED EMBODIMENTS

Figure 1:
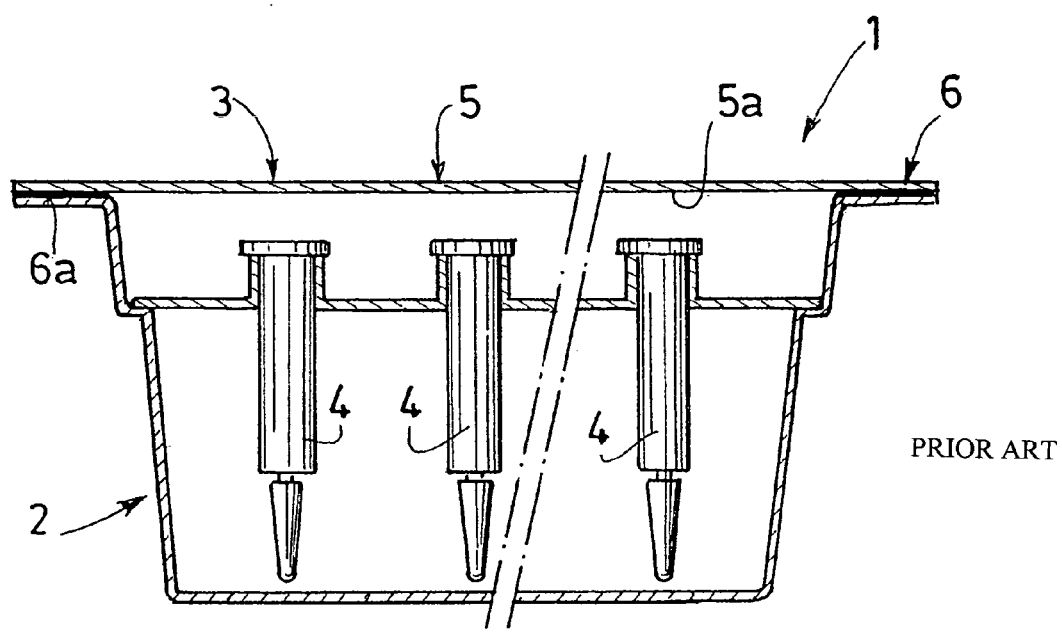
FIG. 1 is a cross section view of a packaging intended to undergo the decontamination process of the invention.
Figure 2:
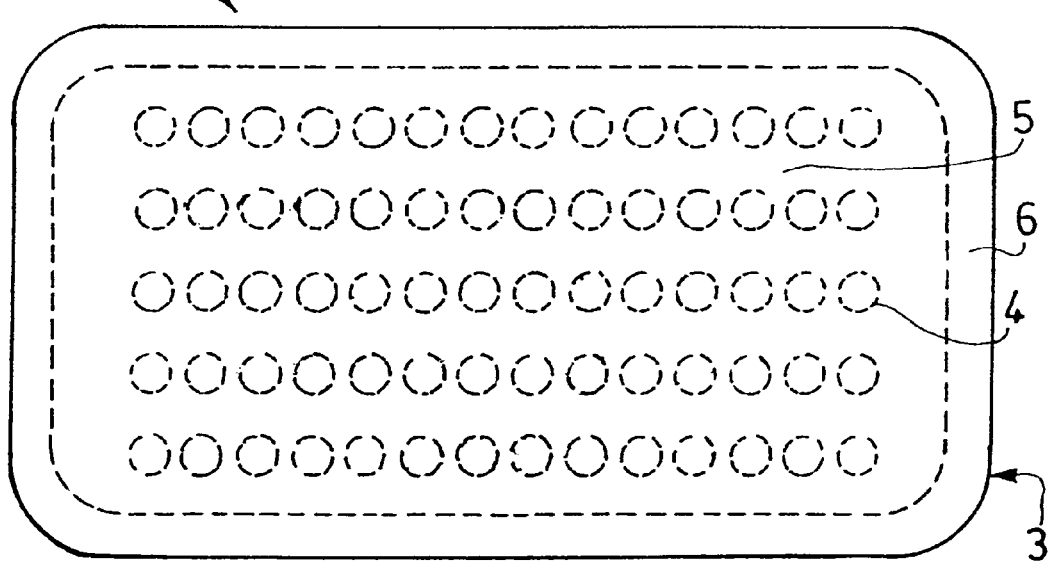
FIG. 2 is a top view of the packaging of FIG. 1, FIGS. 3 to 6 are top views of four steps of the process of the invention.

FIGS. 1 and 2 are already described above. In the following description of FIGS. 3 to 10, the product 1 to be sterilized by the different embodiments of the process of the invention is a packaging 1 according to FIGS. 1 and 2. In consequence, the references used to designate the different elements of the packaging 1 of FIGS. 1 and 2 are maintained in the description of FIGS. 3 to 10. In the example shown, the cover sheet 3 of the packaging 1 is made of a selectively impervious material such as a layer of filaments of a high density polyethylene bound together by heat and pressure, such as the product sold by the Company Du Pont under the trademark "TYVEK®". In the example shown the syringe bodies 4 are made out of glass.

In reference to FIGS. 3 to 6, the packaging 1 is to be sterilized according to a first embodiment of the process with an equipment 100 according to the invention. As shown on FIG. 3, the equipment 100 comprises a first radiation generator which is a high radiation generator 10 and a second radiation generator which is a low radiation generator 11. In particular, the high radiation generator 10 is capable of emitting a high radiation level, for example a high energy electron beam, for instance ranging from 25 kGy to 50 kGy. A high radiation generator 10 suitable for the present invention is for example the generator "Kevac" supplied by the company La Calhène and ranging from 150 to 250 kVolts. The low radiation generator 11 is capable of emitting a low radiation level, for example a low energy electron beam, for instance ranging from 10 kGy to 30 kGy. A low radiation generator 11 suitable for the present invention is for example a generator "Kevac" supplied by the company La Calhène and ranging from 80 to 150 kVolts.

In an embodiment of the invention, the packaging 1 is placed on a conveyor (not shown) and is moved with respect to the high and low radiation generators (10, 11) which are immobile. In an alternative embodiment of the process of the invention, the packaging 1 is fixed and the high and low generators (10, 11) move relative to the packaging 1.

On the example shown on FIGS. 3 to 6, the high and low generators (10, 11) are fixed and the packaging 1 moves from the right of the figures to the left.

Figure 3:
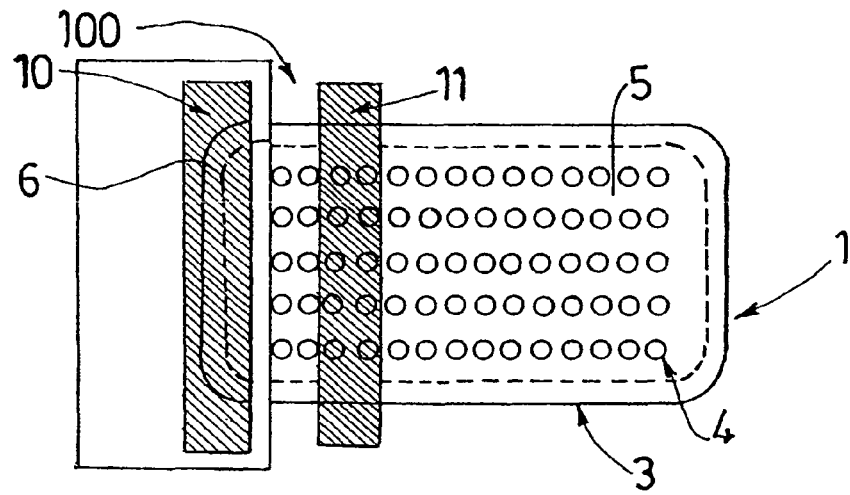

On FIG. 3, at the beginning of the process of the invention, the low radiation generator 11 is vis-à-vis of the central area 5 of the packaging 1, which is situated above the syringe bodies 4, which are shown in dashes and of part of the peripheral outline 6. Low radiation generator 11 emits a low radiation level towards the central area 5 and part of the peripheral outline 6 in order for them to receive, for example, a radiation level of 25 kGy. Such a low level of radiation does not alter the integrity of the syringe bodies 4 contained in the packaging 1. At the same time, the high radiation generator 10, which is spaced away from the low radiation generator 11, is vis-à-vis of part of the peripheral outline 6 of the cover sheet 3, where a high radiation level is needed to decontaminate the top, the inner and the downside (not visible) of the peripheral outline 6 of the cover sheet 3, at the sealing zone with the tub 2. At this stage of the process of the invention, the high radiation generator 10 emits a high radiation level for the part of the peripheral outline 6 to receive, for example, a radiation level of 40 kGy.

Figure 4:
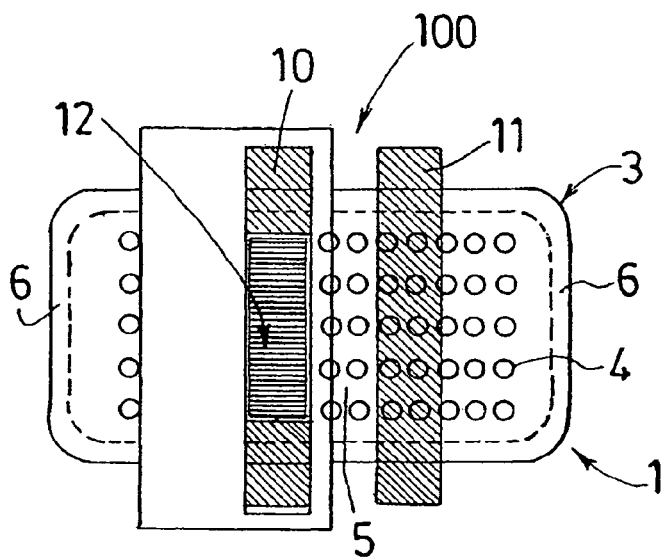

FIG. 4 shows the equipment 100 of the invention and the packaging 1 once the packaging 1 has moved a little forward. At this stage of the process of the invention, the low radiation generator 11 is vis-à-vis of further part of the central area 5 and of the peripheral outline 6 and it continues to emit the low radiation level for the parts of the central area 5 and of the peripheral outline 6 to receive a radiation level of 25 kGy. The high radiation generator 10 is now also vis-à-vis of a part of the central area 5 of the cover sheet 3 and of a part of the peripheral outline 6. A radiation screen 12 is now provided between the high radiation generator 10 and the central area 5 to prevent the high radiation level emitted by the high radiation generator 10 to damage the syringe bodies 4 situated below the central area 5 of the cover sheet 3. The radiation screen 12 may be chosen in the group of, for example, stainless steel, aluminium, thick plastic plate. Such a radiation screen 12 reflects or absorbs substantially all the kinetic energy of the electrons from the electron beam of the high radiation level emitted by the high radiation generator 10, and therefore prevents these electrons from passing through it. In the example, the radiation screen 12 is connected to the high radiation generator 10 and collapsible in order to be placed between the high radiation generator 10 and the packaging 1 before the central area is submitted to high level radiations. In another example not shown, the radiation screen can be mobile and moves along with the packaging in regards to the high and low radiation generators. As appears clearly on FIGS. 4 and 5, the radiation screen 12 is dimensioned so as to be in regard to the central area 5 only and so as to leave the peripheral outline 6 on the lateral side of the cover sheet 3 free of any screen, so that said peripheral outline 6 is able to receive the high radiation level emitted by the high radiation generator 10.

Figure 5:
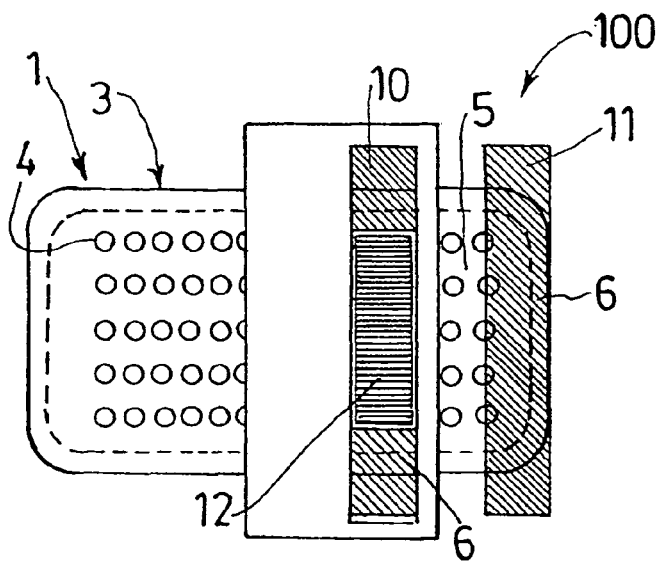

FIG. 5 shows the equipment 100 of the invention and the packaging 1 once the packaging 1 has moved a little forward with respect to FIG. 4. The low radiation generator 11 is now vis-à-vis of the peripheral outline 6 of the cover sheet 3 while the high radiation generator 10 is still vis-à-vis of the central area 5 which is protected from the high radiation level emitted by the high radiation generator 10 by the radiation screen 12.

Figure 6:
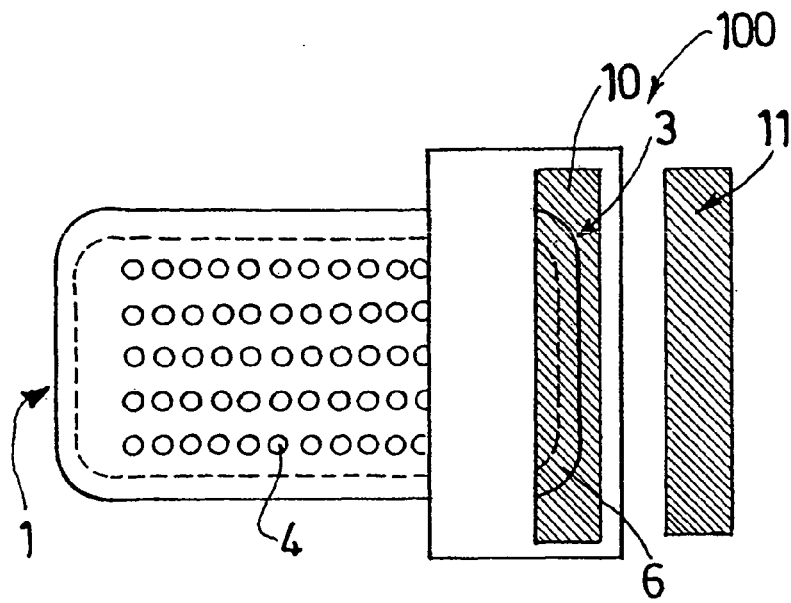

FIG. 6 shows the equipment 100 of the invention and the packaging 1 once the packaging 1 has moved forward so that the high radiation generator 10 is again vis-à-vis of the peripheral outline 6 of the cover sheet 3. At this stage of the process of the invention, the radiation screen 12, which was removably fixed to the high radiation generator 10, is removed. The peripheral outline 6 is then allowed to receive the high radiation level emitted by the high radiation generator 10.

As not shown on the drawing, the lateral sides and downside of the product are also submitted to radiation level emitted by additional radiation generators, for example a low radiation level of 25 kGy.

With the process of the invention described in FIGS. 3 to 6, the central area 5 of the product 1 has undergone only a low radiation level of 25 kGy. The peripheral outline 6 of the product 1 has undergone a high radiation level of 40 kGy. Therefore, the packaging 1 is decontaminated without altering the syringe bodies 4 it contains. In particular, it has been shown that the peripheral outline 6, and especially the downside 6a of such peripheral outline (see FIG. 1), is perfectly decontaminated.

In another embodiment of the invention, the peripheral outline 6 and the central area 5 may be submitted to a same level of radiation emission but for different periods of time, for example by varying the speed displacement of an only radiation generator related to the packaging. In this case, the speed can be chosen lower when two sides of the peripheral outline 6 are submitted to the radiation and higher when the central area 5 is submitted to the radiation. The product can be have a second passage under radiation generator after having been rotated by 90° in order to expose the two other sides of the peripheral outline to a small speed during radiation. The speed difference and the radiation intensity are chosen accordingly to a formula in order to reach, for example, a radiation level of 25 kGy received by the central area 5 and a radiation level of 40 kGy received by the peripheral outline.

In an embodiment of the invention not shown, the central area 5 of the product 1 is protected by a semi-permeable radiation screen. In consequence, when the high radiation generator 10 is vis-à-vis of the central area 5, a certain percentage of the electron beams is allowed to pass through the semi-permeable radiation screen, realizing the decontamination of the central area 5 of the cover sheet 3. For example, the semi-permeable radiation screen allows 60% of the electrons of the electron beam to pass through it. For example, for an initial electron beam emitted by the high radiation level generator 10 as above, the central area 5 will undergo only a radiation level of 25 kGy, whereas the peripheral outline 6 will still receive the initial high radiation level of 40 kGy. The semi-permeable radiation screen may be chosen in the group comprising for example, stainless steel, aluminium, thin plastic plate, titanium. In such an embodiment, the low radiation generator 11 is no more necessary and may be removed.

The process of the invention allows the total decontamination of the cover sheet 3, in its central area 5 as well as on its peripheral outline 6 where it is sealed with the tub 2 and where its downside 6a (see FIG. 1) is not in contact with the sealed atmosphere of the inside of the tub 2.

Figure 7:
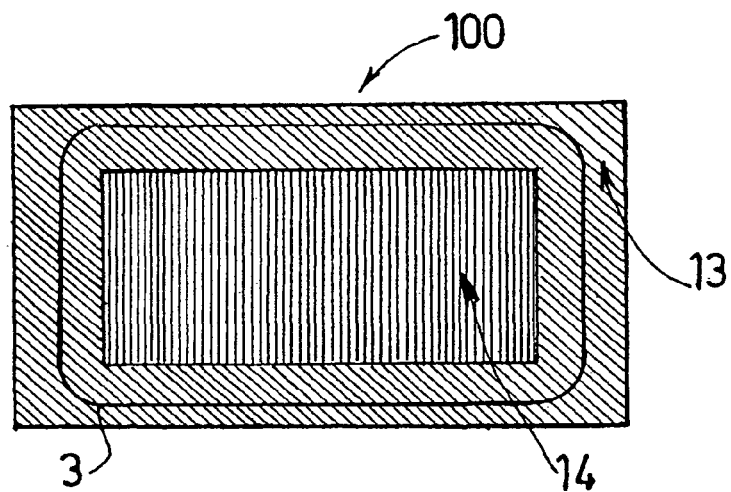
FIG. 7 is a top view of the radiation step of a second embodiment of the process of the invention.

FIG. 7 illustrates a second embodiment of the process of the invention in which the equipment 100 of the invention comprises a single radiation generator which is a variable radiation generator. A variable radiation generator suitable for the present invention is the generator "Kevac" supplied by the company La Cahlène equipped with regulation means. In such a case, two different radiation zones, a high radiation zone 13 and a low radiation zone 14 are defined and the radiation level emitted is variable from a radiation zone to the other. The variation of the radiation level is set by varying the parameters of the electron beam from the generator, in accordance with the following formula:

$$D=k \cdot i \cdot E/(S \cdot W)$$

in which:

k is a multiplier factor,

D is the sterilization dose in kGy, i is the intensity of the electric current in mA (micro Ampère), E is the energy of the electrons in KeV (kilo Electron volts), S is the speed of the rays from the radiation in m/min, W is the width of the rays in cm.

The decontamination dose may therefore be adjusted by varying the speed of the rays or the energy of the electrons or the intensity of the electric current.

Similar results may be achieved by using a combination (not shown) of high and low radiation generators. In this case, the high radiation generator is set to emit radiations according to the high radiation zone 13 and no radiation or very few in the low radiation zone 14. The low radiation generator is set in order to emit radiations according to at least the low radiation zone 14.

Figure 8:
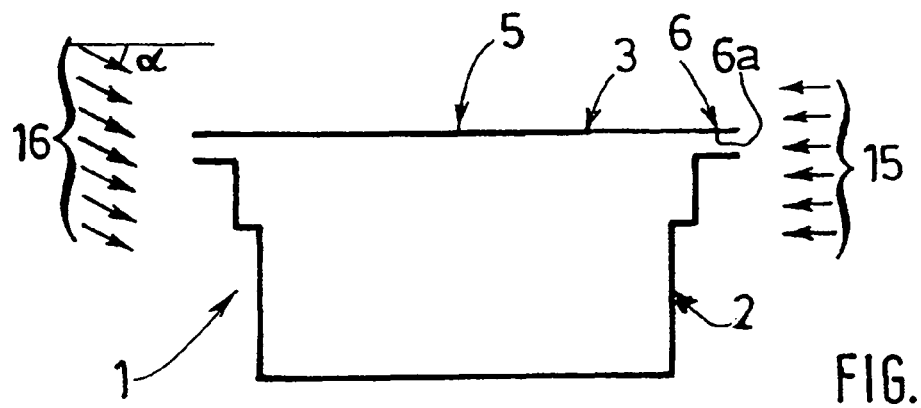
FIG. 8 is a schematic side view of the radiation step of a third embodiment of the process of the invention.

FIG. 8 illustrates in a schematic way another embodiment of the process of the invention in which first and second radiation levels are reached by placing first and second radiation generators at specific angle positions with respect to the peripheral outline 6 and the central area 5. The downside 6a of the peripheral outline 6 of the cover sheet 3 is decontaminated by horizontal rays 15 coming from a first radiation generator (not shown) whereas the central area 5 is decontaminated by oblique rays 16 coming from a second radiation generator (not shown). For example, in the embodiment shown on FIG. 8, the oblique rays 16 may form an angle α of 1 to 45° and preferably from 1 to 10° with the surface of the central area. The lateral walls of the tub 2 protect the syringe bodies (not shown) contained in the tub 2 from being altered by the horizontal and oblique rays (15, 16).

Figure 9:
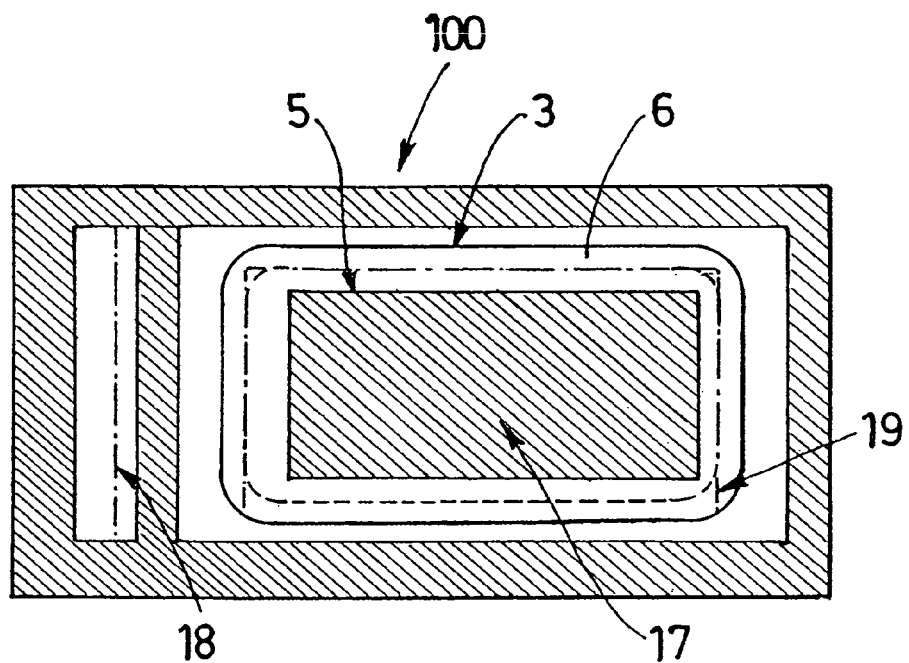
FIG. 9 is a top view of the radiation step of a fourth embodiment of the process of the invention.

FIG. 9 illustrates another embodiment of the process of the invention in which the high radiation level is reached by using a first radiation generator 19 having a shape roughly similar to the peripheral outline 6 and emitting flashes of high level radiation along the peripheral outline 6. The low radiation level is reached using a second radiation generator 18 similar to the low radiation generator 11 of FIGS. 3 to 6. In this example shown, the use of a radiation screen 17 dimensioned to cover substantially all the central area 5 of the cover sheet 3 is optional. The radiation screen 17 may be chosen from the group comprising, for example, stainless steel, aluminium, thick plastic plate. The equipment 100 of the invention is provided with a continuous electric strand 18 which acts as a low radiation generator and creates a low radiation level such as a low energy electron beam in order to decontaminate the central area 5 of the cover sheet 3. The equipment 100 is also provided with a flash electric strand 19 which runs along the peripheral outline 6, forming a rectangle, and which acts as a high radiation generator by creating a high radiation level such as a high energy electron beam in order to decontaminate the peripheral outline 6 of the cover sheet 3. During the emission of the high radiation level by the flash electric strand 19, the central area 5 can be protected by the radiation screen 17 and the syringe bodies contained in the packaging 1 are not altered.

Figure 10:
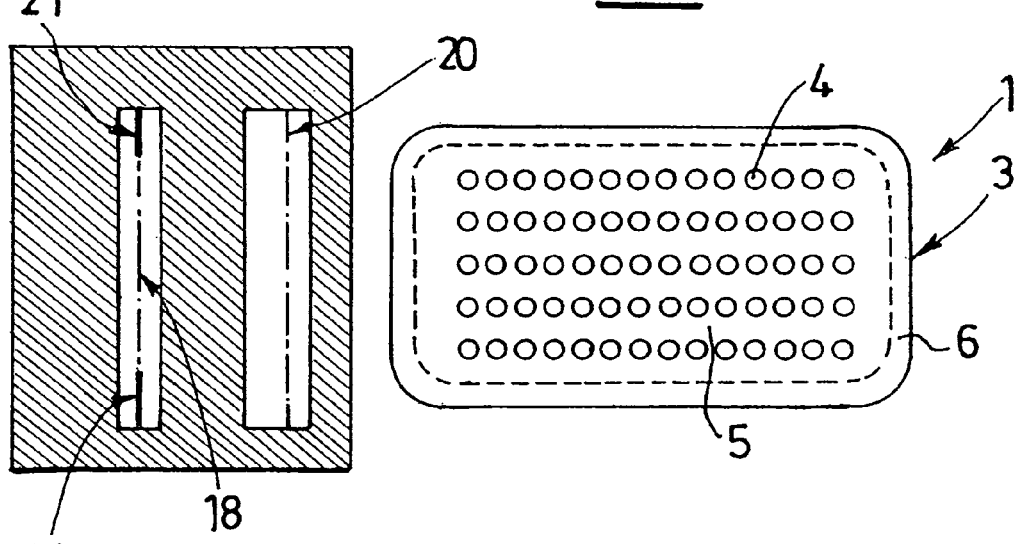
FIG. 10 is a top view of the radiation step of a fifth embodiment of the process of the invention.

FIG. 10 illustrates an alternative of the embodiment of the invention shown on FIG. 9. In this embodiment, the rectangular flash electric strand of the equipment 100 of FIG. 9 is replaced by linear high electric strands 21 able to emit a high radiation level and potentially combined and separated by a linear low electric strand 18 to emit low radiation level. The equipment 100 further comprises a continuous electric strand 20 which creates a low radiation level like in the embodiment of FIG. 9. The lateral parts of the peripheral outline 6 are then submitted to the high radiation level from the linear high electric strands 21 and the extremity parts of the outline 6 are submitted to a high radiation level reached by the addition of the low radiation level emitted by the linear low electric strand 18 and the low radiation level emitted by the continuous electric strand 20. The central area is submitted to the low radiation level emitted by the continuous electric strand 20.

The process of the invention and the equipment of the invention allow the efficient decontamination of a first part of a product, such as a packaging for medical items, and of a second part of said product, without altering the integrity of the contents of the product such as medical items, and regardless from the shape of said product and/or packaging. They also enable to efficiently decontaminate any kind of other products for which it is required to expose one of its parts to a lower radiation level than the other parts of it.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. Process for decontamination by radiation of a product, comprising at least one exposing step during which at least one radiation generator is used to expose at least a first part of said product to a first radiation level and at least a second part of said product to a second radiation level, an external surface of one side of said product comprises a central area and a peripheral outline, said first part of said product comprises at least said peripheral outline and said second part of said product comprises at least said central area, such that said peripheral outline is radiated at said first radiation level and said central area is radiated at said second radiation level, said first radiation level being higher than said second radiation level.

2. The process according to claim 1, wherein doing said exposing step, said first part and second part are successively exposed to said first and second radiation levels.

3. The process according to claim 1, wherein during said exposing step, said first part and second part are simultaneously exposed to said first and second radiation levels.

4. The process according to claim 1, wherein said first and second radiation levels are reached by using at least a high radiation generator omitting a high radiation level, and a low radiation generator emitting a low radiation level.

5. The process according to claim 1, wherein said first and second radiation levels are reached by using at least a long radiation exposition period and a short radiation exposition period, respectively, toward said first and second parts of said product.

6. The process according to claim 5, wherein said short and long radiation exposition periods are reached by using two different displacement speeds of said product relative to said radiation generator.

7. The process according to claim 1, wherein said first and second radiation levels are reached by using at least one variable radiation generator set to emit a first radiation level toward said first part of said product and a second radiation level toward said second part of said product.

8. The process according to claim 1, wherein said first and/or second radiation levels are reached by using a radiation generator having a shape roughly similar to said first and/or second part of said product.

9. The process according to claim 1, wherein said first and second radiation levels are reached by using at least a high radiation generator to emit high radiation level toward said product placing a radiation screen or semi-permeable radiation screen between said high radiation generator and said second part of said product.

10. The process according to claim 9, wherein said radiation screen or semi-permeable radiation screen is fixed with respect to said second part of said product.

11. The process according to claim 9, wherein said high radiation generator is mobile with respect to said product and said radiation screen or semi-permeable radiation screen is removably fixed to said high radiation generator.

12. The process according to claim 1, wherein said first and second radiation levels are reached by placing at least a first radiation generator and a second radiation generator at specific angle positions with respect to the first and second parts of said product.

* * * * *